United States Patent [19]

Buckler et al.

[11] Patent Number: 4,650,771
[45] Date of Patent: Mar. 17, 1987

[54] IMMUNOGENS, ANTIBODIES, LABELED CONJUGATES, AND RELATED DERIVATIVES FOR LIDOCAINE AND ANALOGS THEREOF

[75] Inventors: Robert T. Buckler, Edwardsburg, Mich.; John F. Burd, Mountain View, Calif.; Stephan G. Thompson, South Bend, Ind.

[73] Assignee: Miles Laboratories, Inc., Elkhart, Ind.

[21] Appl. No.: 548,647

[22] Filed: Nov. 4, 1983

[51] Int. Cl.$^4$ .................. G01N 33/536; A61K 39/00
[52] U.S. Cl. ........................... 436/536; 424/88; 435/7; 436/543; 436/544; 436/547; 436/815; 436/822; 436/823; 530/387; 530/403
[58] Field of Search ................ 435/7; 436/86, 140, 436/543, 544, 547, 823, 536, 815, 822; 424/88; 530/387, 403

[56] References Cited

U.S. PATENT DOCUMENTS

| | | | |
|---|---|---|---|
| 4,069,105 | 1/1978 | Singh | 436/517 X |
| 4,213,894 | 7/1980 | Buckler | 436/823 X |
| 4,235,969 | 11/1980 | Singh et al. | 436/823 X |
| 4,243,608 | 1/1981 | Varma et al. | 436/823 X |
| 4,331,590 | 5/1982 | Bocuslaski et al. | 436/823 X |
| 4,469,797 | 9/1984 | Albarella | 436/536 |
| 4,486,344 | 12/1984 | Buckler | 260/121 |
| 4,495,281 | 1/1985 | Buckler et al. | 435/7 |

OTHER PUBLICATIONS

Nelson, et al., J. Pharm. Sci., vol. 66, No. 8, (1977), pp. 1180-1190.
Butler, V., J. Immunol. Meth., vol. 7, (1975), pp. 1-24.
Strong, et al., Clin. Pharm. Ther., vol. 14, No. 1, (1973), pp. 67-72.
Dutton, et al., Biochem. Biophys. Res. Comm., vol. 23, No. 5, (1966), pp. 730-739.
Frohman, et al., Endocrinology, vol. 87, (1970), pp. 1055-1061.
Welsh, K., Nature, vol. 266, No. 7, (1977), p. 495.
Dandliker, et al., J. Exp. Med., vol. 122, (1965), pp. 1029-1048.
Cuatrecasas, et al., J. Biol. Chem., vol. 244, No. 2, (1969), pp. 406-412.
Strong, et al., Anal. Chem., vol. 44, No. 14, (1972), pp. 2287-2290.
Zipes, et al., American J. Cardiology, vol. 41, (1978), pp. 1005-1024.
Burney, et al., American Heart Journal, vol. 88, No. 6, (1974), pp. 765-769.
Winkle, et al., American J. Cardiology, vol. 36, (1975), pp. 629-650.
Gianelly, et al., New Eng. J. Med., vol. 277, No. 23, (1967), pp. 1215-1218.
Blumer, et al., J. Pharm. Exp. Therap., vol. 186, No. 1, (1973), pp. 31-36.
Dusci, et al., Clin. Tox., vol. 14, No. 5, (1979), pp. 587-592.
Lee, et al., J. Chromatography, vol. 158, (1978), pp. 403-410.
Lehane, et al., Clin. Chem. vol. 25, No. 4, (1979), pp. 614-616.

List Continued on next page.

Primary Examiner—Christine M. Nucker
Assistant Examiner—Stephen C. Wieder
Attorney, Agent, or Firm—Andrew L. Klawitter; Daniel W. Collins

[57] ABSTRACT

Immunogens for preparing antibodies against the drug lidocaine and related compounds, labeled conjugates, synthetic intermediates, and the use of such antibodies and labeled conjugates in immunoassays for determining lidocaine and such related compounds. The immunogens comprise lidocaine or an analog thereof coupled through one of the aromatic methyl groups to a conventional immunogenic carrier. The antibodies and labeled conjugates are particularly useful in homogeneous non-radioisotopic immunoassays for measuring lidocaine or its analogs in biological fluids such as serum.

25 Claims, 1 Drawing Figure

OTHER PUBLICATIONS

Weinryb, et al., Drug Metabolism Reviews, vol. 10, No. 2, (1979), pp. 271–283.

Playfair, et al., Br. Med. Bull., vol. 30, (1974), pp. 24–31.

Broughton, et al., Clin. Chem., vol. 22, No. 6, (1976), pp. 726–732.

Butler, V., J. Immunol. Meth., vol. 7, (1975), pp. 1–24.

Elderfield, et al., J. Am. Chem. Soc., vol. 68, (1946), pp. 1568–1569.

Donohue, et al., J. Org. Chem., vol. 22, (1957), pp. 68–70.

Linnell, et al., J. Pharm. Pharmacol., vol. 4, (1952), pp. 55–65.

Hurd, et al., J. Am. Chem. Soc., vol. 74, (1952), pp. 5324–5329.

Barger, et al., J. Chem. Soc., 1937, pp. 714–718.

Keller, et al., Helvetica Chimica Acta, vol. 58, Fasc. 2, (1975), pp. 531–541.

Kitagawa, et al., J. Biochem., vol. 79, (1976), pp. 233–236.

Carlsson, et al., Biochem. J., vol. 173, (1978), pp. 723–737.

Buckler, et al., Eur. J. Med. Chem.–Chimica Therapeutica, vol. 12, No. 5, (1977), pp. 463–465.

Martin, et al., Biochemistry, vol. 20, (1981), pp. 4229–4238.

Kay, et al., Nature, vol. 216, (1967), pp. 514–515.

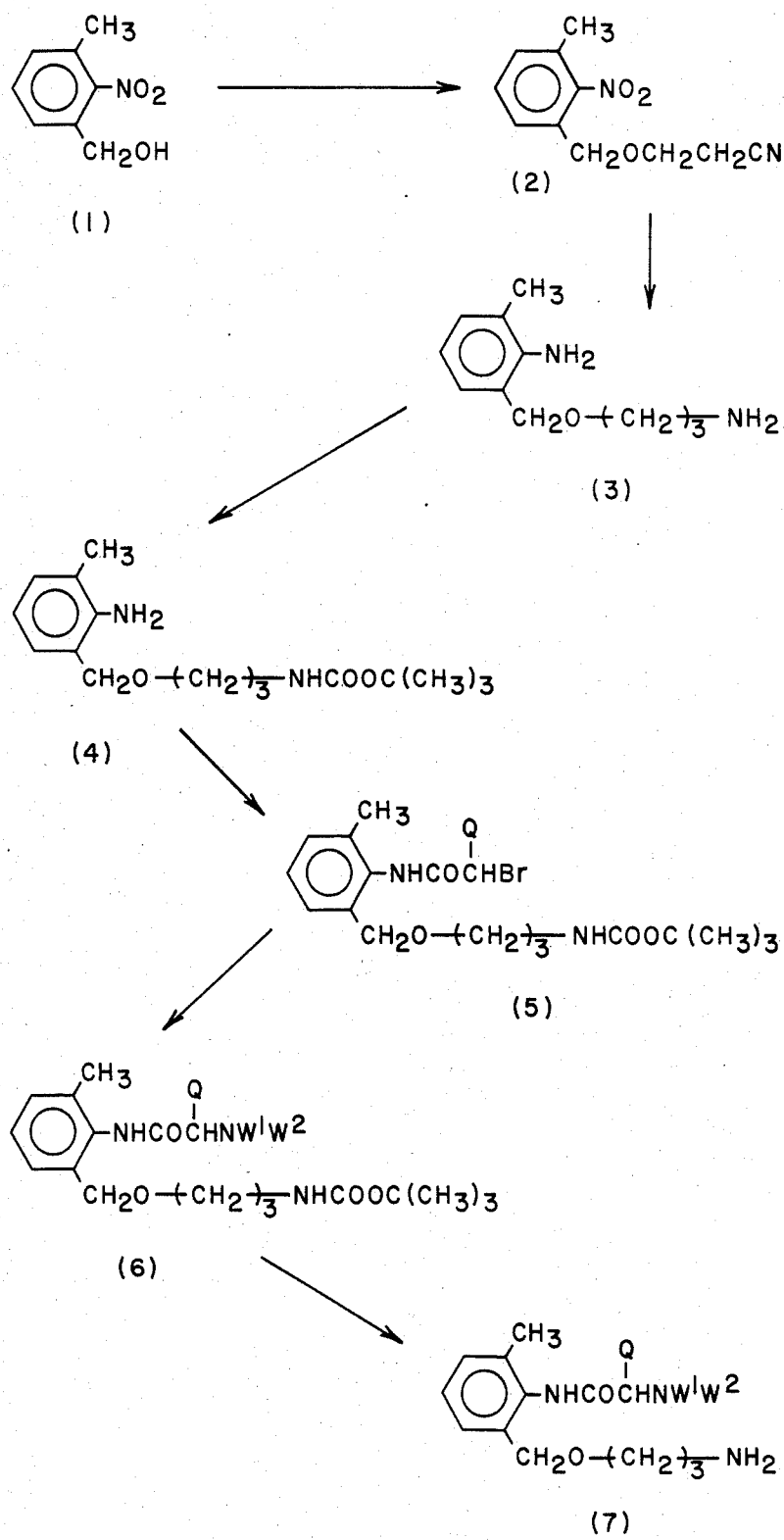

IMMUNOGENS, ANTIBODIES, LABELED CONJUGATES, AND RELATED DERIVATIVES FOR LIDOCAINE AND ANALOGS THEREOF

BACKGROUND OF THE INVENTION

1. Field of the Invention

This invention relates to novel derivatives of lidocaine and related compounds (analyte) pertaining to immunoassays in liquid media such as biological fluids. Such derivatives include immunogens used to stimulate production of antibodies to the analyte of interest in host animals by conventional techniques. Also provided are labeled conjugates used as reagents, along with the antibodies, in particularly preferred immunoassays. Intermediates in the synthesis of the aforementioned immunogens and labeled conjugates are also provided.

Lidocaine [Merck Index, 9th ed., p. 5331 (1976)] is a local anesthetic of the formula:

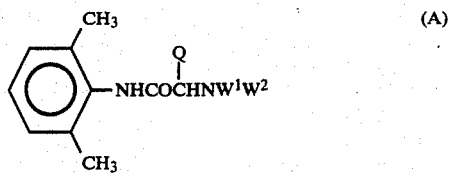

(A)

where Q is hydrogen and $W^1$ and $W^2$ are both ethyl, which also possesses antiarrhythmic properties, particularly against ventricular arrhythmias. It is widely used in the treatment of post-myocardial infarction patients where it is administered by bolus injection of 1 to 2 milligrams per kilogram, followed by constant infusion at a dose level of 20 to 50 micrograms per kilogram per minute. The toxic side effects hypotension, CNS depression, and convulsions appear to be avoidable if the blood levels do not exceed 5 micrograms per milliliter (ml). On long term constant infusions, 24 to 36 hours may be required to reach a steady state. Patients receiving such therapy need to be observed carefully and continuously for signs of lidocaine toxicity. Lidocaine and possibly lidocaine metabolite blood levels may have to be determined in order to treat arrhythmias effectively and fully understand the toxicity of the drug in a given patient. [Gianelly et al, New Engl. J. Med. 277: 1215 (1967); Winkle et al, Amer. J. Cardiology 36: 629 (1975)].

Lidocaine is metabolized in the liver by N-deethylation to produce monoethyl glycine xylidide [MEGX, formula (A) where Q=hydrogen, $W^1$=ethyl, $W^2$=hydrogen], and glycine xylidide [GX, formula (A) where $Q=W^1=W^2$=hydrogen]. In one study, the former metabolite was found to occur in blood in a concentration range of 0.31 to 2.6 micrograms per ml and was 80% as potent as an antiarrhythmic as lidocaine. The completely deethylated derivative (GX) was only one-tenth as potent as the parent drug [Burney et al, Amer. Heart J. 88: 765 (1974)]. In humans, elevated blood levels of MEGX have been linked with the central nervous system (CNS) side effects associated with lidocaine therapy. In rats the median convulsant dose of MEGX was determined to be 67 milligrams (mg) per kilograms as compared to 52 mg per kilogram for lidocaine itself, which suggests that the occurrence of seizures in humans treated with lidocaine may be partially due to the metabolite MEGX [Blumer et al, J. Pharm. Exp. Therap. 186: 31 (1973); Strong et al, Clin. Pharm. Therap. 14: 67 (1973)].

Tocainide, a primary amide analogue of lidocaine [formula (A) where Q is methyl and $W^1=W^2$=hydrogen], also possesses similar antiarrythmic properties and toxicity characteristics. Unlike lidocain, tocainide can be administered orally since it is not rapidly metabolized and eliminated in the first pass through the liver. Tocainide has a 10 hour half-life, is therapeutic at serum concentrations of 6 ng/ml, and has been used in combination with either quinidine or disopyramide. [Zipes and Troup, Amer. J. Cardiol. 41: 1005–1024 (1978)].

For optimum therapeutic management of patients medicated with the above-discussed drugs and metabolites, a rapid and specific analytical method is needed that is sensitive enough to measure plasma concentrations of the drug. This need has led to the development of a variety of analytical procedures to determine blood levels, particularly for lidocaine and MEGX. Some examples are mass fragmentography [Strong and Atkinson, Anal. Chem. 44: 2287 (1972)]; gas-liquid chromatography [Dusci and Hacket, Clin. Toxicol. 14: 587 (1979)]; high performance thin layer chromatography [Lee et al, J. Chromat. 158: 403 (1978)]; and enzyme-mediated immunoassay [Lebane et al, Clin. Chem. 25: 614 (1979)].

The preparation of antibodies to lidocaine and its analogs for use in immunoassays has been accomplished in the prior art by forming a particular immunogen conjugate of the drug and a conventional immunogenic carrier material and injecting such immunogen into the bloodstream of an appropriate host animal to stimulate antibody production. U.S. Pat. No. 4,069,105 describes such immunogen conjugates wherein the drug is coupled to the carrier through an imine linkage attached to one of the three unsubstituted positions on the lidocaine phenyl group. Specifically exemplified is attachment at the unsubstituted position which is para to the native amide side chain in the drug. Derivation of lidocaine at such para position through a different linkage for the purpose of forming labeled conjugates useful in a certain inhibitor-labeled immunoassay is proposed in U.S. Pat. No. 4,273,866.

The state-of-the-art of preparing antibodies to haptens such as drugs is represented by Weinryb et al, Drug Metabolism Reviews 10: 271 (1975); Playfair et al, Br. Med. Bull. 30: 24 (1974); Broughton et al, Clin. Chem. 22: 726 (1976); and Butler, J. Immunol. Meth. 7: 1 (1976) and Pharmacol. Rev. 29(2): 103 (1978).

Labeled conjugates, comprising the analyte or a derivative or other analog thereof, coupled to a labeling substance are variously described in the literature, e.g., U.S. Pat. Nos. 4,279,992; 4,182,856; 4,259,233; and 4,292,425 wherein the label is the fluorogenic enzyme substrate β-galactosylumbelliferone, and U.S. Pat. No. 4,213,893, wherein the label is flavin adenine dinucleotide.

SUMMARY OF THE INVENTION

The present invention uniquely provides reagents for use in immunoassays to determine lidocaine and particular analogs thereof such as MEGX, GX, and tocainide, referred to collectively herein as analyte, involving the coupling to or derivatization of the analyte at one of the native methyl substituents on the phenyl ring. The immunogen of the present invention, comprising the haptenic analyte chemically linked through such aromatic methyl substituent to a conventional immunogenic carrier material, stimulates the production of antibodies to the analyte. By coupling the analyte at this position, where no metabolism occurs and no significant immunological distinguishing substituents appear, immunogen conjugates are prepared without significant modification of the analyte.

The present invention also provides novel intermediates in the synthesis of the methyl-substituted analyte reagents. Additionally, there are provided an improved immunoassay method and reagent system for the determination of the analyte using the novel antibodies of the present invention. Further, the present invention provides labeled analyte conjugates for particularly preferred embodiments of such immunoassay method and system.

BRIEF DESCRIPTION OF THE DRAWING

The drawing illustrates a particular synthetic scheme for preparing aromatic methyl derivatives of lidocaine and its analogs used in the present invention.

DESCRIPTION OF THE PREFERRED EMBODIMENTS

The present invention focuses on the preparation of derivatives of lidocaine and its methyl amine analogs modified at one of the aromatic methyl substituents. Such derivatives are then used to form immunogens by coupling to conventional carrier materials, and subsequently used to obtain antianalyte antibodies, or are used to form labeled conjugates which serve as detection reagents in selected types of immunoassays.

AROMATIC METHYL DERIVATIVES

The analyte derivatives of the present invention are of the general formula:

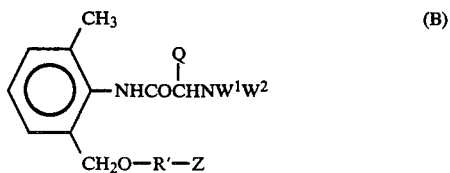

(B)

wherein Q is hydrogen or lower alkyl, $W^1$ and $W^2$, which can be the same or different, are selected from hydrogen and lower alkyl, R' is a chemical bond or an appropriate linking group, and Z is a reactive functional group capable of being coupled to a selected immunogenic carrier material or labeling reagents as more fully described below.

As used herein, lower alkyl shall mean substituted and unsubstituted hydrocarbon residues of the formula $-C_mH_{2m+1}$ wherein m is an integer from 1 through 6, thereby including linear and branched forms (e.g., methyl, ethyl, n-propyl, iso-propyl, n-butyl, isobutyl, tert-butyl, n-hexyl, and so forth) with linear forms being preferred and with m less than or equal to 4 also being preferred. Such derivatives are formed by alkylation of the starting material 3-hydroxymethyl-2-nitrotoluene (1). Alkylation of the hydroxyl group of (1) can be accomplished by any convenient method, for instance, by reaction with the reagent X—R'—Z' where X is an appropriate leaving group such as chloro, bromo, iodo, paratoluenesulfonyl, methanesulfonyl, and the like, and where Z' is Z or a group which can be converted into Z, e.g., phthalimide which can be converted to amino by treatment with hydrazine and carboxyester which can be converted to carboxyl. Functional group Z' commonly is amino, carboxyl, thiol, hydroxyl, or maleimido, or a protected form or precursor thereof. The only critical feature of the reagent X—R'—Z' is that leaving group X be attached to R' in such a way that it will undergo a typical nucleophilic displacement upon reaction with the hydroxyl group in starting material (1). Examples of alkylating reagents X—R'—Z' are those comprising elements selected from any combination of the following:

| X | R' | Z' |
|---|----|----|
| $CH_3SO_3^{\oplus}$ | $+CH_2)_{\overline{n}}$ | $CF_3CONH-$ |
| $CH_3-\langle\bigcirc\rangle-SO_3^{\ominus}$ | $\langle\bigcirc\rangle-CH_2-$ <br> $(CH_2)_{\overline{3}}$ | $C_2H_5OOC$ |
| Cl | | $CH_3COO-$ |
| Br | $-CH_2CH=CHCH_2-$ <br> $+CH_2)_{\overline{z}}O+CH_2)_{\overline{z}}$ | phthalimido group |

It is evident that one skilled in the art has a wide variety of linking groups R' that can be introduced into the derivatives of the present invention. Exemplary of such choices are linear and branched alkylenes comprising from 1 to as many as 15, more usually 10 or less, and normally less than 6, carbon atoms (e.g., methylene, ethylene, n-propylene, isopropylene, n-butylene, and so forth). In addition, such alkylenes can contain other substituent groups such as cyano, amino, (including substituted amino), acylamino, halogen, thiol, hydroxyl, carbonyl groups, carboxyl (including substituted carboxyls such as esters, amides, and substituted amides), providing, of course, that any such functional group not interfere with the subsequent synthetic steps, particularly the coupling to carrier materials or labeling reagents. The linking group R' can also contain or consist of substituted or unsubstituted aryl, aralkyl, or heteroaryl groups (e.g., phenylene, phenethylene, and so forth). Additionally, such linkages can contain one or more heteroatoms selected from nitrogen, sulfur and oxygen in the form of ether, ester, amido, thio ether, amidino, sulfone, or sulfoxide. Also, such linkages can include unsaturated groupings such as olefinic or acetylenic bonds, imino, or oximino groups. Preferably R' will be a chain, usually an aliphatic group, comprising between 1 and 20 atoms, more usually between 1 and 10, excluding hydrogen, of which between 0 and 5 are heteroatoms selected from nitrogen, oxygen, and sulfur. Particularly preferred are the derivatives wherein R' is $-(CH_2)_{\overline{n}}$ with n being an integer from 1 through 10 and wherein Z is amino or carboxyl, or a protected form thereof. Therefore, the choice of linking group R' is not critical to the present invention and may be selected by one of ordinary skill taking normal precautions to assure that stable compounds are produced.

Examples of synthetic routes available to obtain analyte derivatives (B) having such linking groups R' and terminal functional groups Z' follow.

Following the procedure outlined above, the benzyl alcohol starting material (1) can be alkylated with omega-bromoalkyl phthalimides to give derivatives (B) where R' is $-(CH_2)_{\overline{n}}$ and Z' is phthalimido, a protected form of NH₂, which can be converted to NH₂ by reaction with hydrazine. Such bromo-phthalimides where n=5-9 are known compounds [cf. Dirscher and Weingarten, *Ann.* 574: 131 (1951); Muller and Krauss, *Montash.* 61: 219 (1932); Elderfield et al, *J. Am. Chem. Soc.* 68: 1568 (1946); Donahue et al, *J. Org. Chem.* 22: 68 (1957)].

Starting material (1) can also be alkylated with omega-bromoalkanoic acid esters to give derivatives (B) where R' is —(CH₂)ₙ— and Z' is —COOC₂H₅, a precursor of —COOH. Ethyl omega-bromoesters where n=1 through 4 are commercially available; n=5 through 9 are known compounds [cf. Barger et al, *J. Chem. Soc.* (1937), 714; Salmon-Legagneur, *Bull. Soc. Chem. France*, (1956), 411; Linnell and Vora, *J. Pharm. Pharmacol.* 4: 55 (1952)].

In addition, the benzyl alcohol (1) can be alkylated with omega-haloalkanals which are available from the class of omega-hydroxyaldehydes [Hurd et al, *J. Am. Chem. Soc.* 74: 5324 L (1952)], to give derivatives (D) having R'=—(CH₂)ₙ— and Z'=CHO.

Examples of derivatives (B) where Z is thiol can be obtained by reacting a derivative (B) where Z=NH₂ with N-succinimidyl-3-(2-pyridyldithio)propionate and reducing the product, usually in situ, to the free thiol compound [cf. Carlsson et al, *Biochem. J.* 173: 723 (1978)].

Derivatives (B) functionalized with maleimido groups can be prepared by reacting a derivative (B) where Z=NH₂ with maleic anhydride and cyclizing the product to form the maleimido group. Alternatively, amino derivatives can be reacted with maleimido substituted carboxylic acids to give maleimido-substituted derivatives in which the original linking group R' present in the amines have been extended to include the amide function contributed by the maleimido carboxylic acid. Examples of the latter are known [Kitagawa and Aikawa, *J. Biochem.* 79: 233 (1976); Keller and Riedinger, *Helv. Chim. Acta* 58: 531 (1975)].

Similarly, the linking group R' can vary widely. For example, an unsaturated linkage can be inserted by reacting the benzyl alcohol starting material (1) with N-(4-bromobutenyl)phthalimide [Birkofer and Hempel, *Chem. Ber.* 93: 2282 (1960)].

A phenylene linking group can be introduced by alkylating the starting material (1) with 2-(3-chloropropyl)benzyl chloride to give derivatives (B) wherein

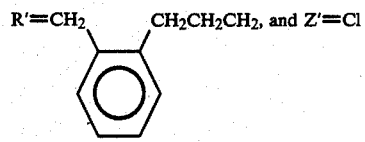

R'=CH₂ CH₂CH₂CH₂, and Z'=Cl which can be further transformed to the carboxyl derivative, Z=COOH, by reaction with cyanide ion and treatment with acid [cf. Buckler et al, *Europ. J. Med. Chem.* 12: 463 (1977)].

From the above-described synthetic routes, it is clear that the analyte derivatives of general structure (B), where Z is a reactive group for coupling to an immunogenic carrier material or an appropriate labeling residue, can be prepared with a wide latitude in the nature of linking group R'.

Particularly preferred are analyte derivatives of the formula:

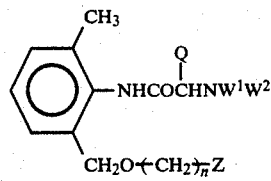

where n is an integer from 1 through 10, usually from 1 through 6, and preferably 3. Derivatives (C) wherein Q is hydrogen or lower alkyl, n=3, and Z=amino can be prepared by the synthetic scheme shown in the drawing and described more fully in the examples. Referring to the drawing, the benzyl alcohol (1) is reacted with acrylonitrile to give the cyanoethyl ether (2). Catalytic hydrogenation of (2) simultaneously reduces both the cyano and the nitro groups to primary amines yielding the diamine (3). Reaction of (3) with 1 equivalent of di-tert-butyl dicarbonate gives the mono-protected intermediate (4). The unprotected aromatic amine group of (4) is then acylated with the desired α-bromoalkanoic acid chloride, and the product (5) is reacted with ammonia or a desired monoalkyl- or dialkylamine to produce (6). In cases where W¹=W²=hydrogen, the primary amine group in (6) is then suitably protected such as by reaction with o-nitrophenylsulfenyl chloride. Removal of the tertbutyloxycarbonyl protecting group by treatment with acid leaves (7) which possesses a primary amino group suitable for subsequent coupling reactions. Where a primary amine group was present in (6) and results in a protected form of (7), such protecting group is removed by treatment with base after the coupling of (7) to an immunogenic carrier, a labeling reagent, and so forth.

IMMUNOGENS

The above-described analyte derivatives (B) can be covalently linked by any number of conventional techniques to immunogenic carrier materials to yield immunogens comprising one or more residues of the formula:

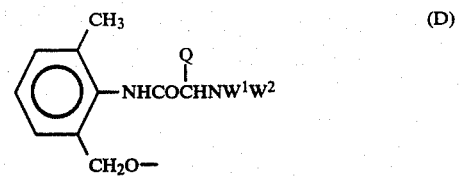

where Q, W¹ and W² are as defined above. More particularly, such immunogens will have the formula:

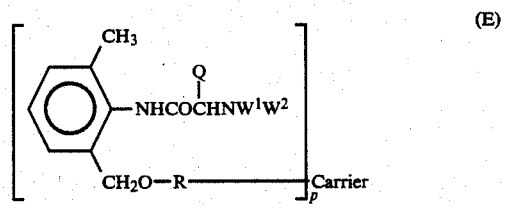

where Carrier is an immunogenic carrier material, R is an appropriate linking group resulting from the coupling of derivatives (B) to the carrier, and p is the number of hapten moieties coupled to the carrier. The number p is sometimes referred to as the epitopic density of the immunogen and is limited only by the number of available coupling sites on the carrier molecule. However, in the usual situation where the carrier is a naturally occurring protein such as albumin, R will be on the average from 1 to about 50, more normally from 1 to about 25. Optimal epitopic densities in such usual case, considering the ease and reproducibility of synthesis of the immunogen and antibody response, fall between about 2 and about 20, more usually between 5 and 15.

The immunogenic carrier material can be selected from any of those conventionally known. In most cases, the carrier will be a protein or polypeptide, although other materials such as carbohydrates, polysaccharides, lipopolysaccharides, nucleic acids and the like of sufficient size and immunogenicity can likewise be used. For the most part, immunogenic proteins and polypeptides will have molecular weights between 5,000 and 10,000,000, preferably greater than 15,000, and more usually greater than 50,000. Generally, proteins taken from one animal species will be immunogenic when introduced into the blood stream of another species. Particularly useful proteins are albumins, globulins, enzymes, hemocyanins, glutelins, proteins having significant nonproteinaceous constituents, e.g., glycoproteins, and the like. The albumins and globulins of molecular weight between 30,000 and 200,000 are particularly preferred. Further reference for the state-of-the-art concerning conventional immunogenic carrier materials and techniques for coupling haptens thereto may be had to the following: Parker, *Radioimmunoassay of Biologically Active Compounds*, Prentice-Hall (Englewood Cliffs, N.J., U.S.A., 1976); Butler, *J. Immunol. Meth.* 7: 1–24 (1975); Weinryb and Shroff, *Drug Metab. Rev.* 10: 271–283 (1975); Broughton and Strong, *Clin. Chem.* 22: 726–732 (1976); Playfair et al, *Br. Med. Bull.* 30: 24–31 (1974); and Butler, *J. Immunol. Meth.* 7: 1 (1976) and *Pharmacol. Rev.* 29(2): 103 (1978).

Appropriate analyte derivatives (B) are couplable to immunogenic carrier materials according to well known techniques. For example, amino derivatives can be coupled to carboxyl-bearing carriers (e.g., protein or polypeptide carriers) by common peptide bond-forming reactions by means of activated esters, acyl azide formation, carbodiimides, etc., see Peptides, ed. Goodman and Meinhofer, John Wiley & Sons (New York, 1977) p. 6 et seq., and *The Peptides, Analysis, Synthesis, Biology*, Vol. 1, Academic Press (New York 1979). The same methods apply likewise for attaching carboxylated derivatives to amino-bearing carriers.

Thiolated derivatives can be attached to thiol-containing polymers (IgG or thiolated proteins) by the disulfide exchange procedure [Martin et al, *Biochem.* 20: 4229 (1981)]. Alternately, an amino-containing polymer can be reacted with the reagent MBS and the product coupled to thiol-containing derivatives by the process described by Kitagawa and Aikawa, *J. Biochem.* 79: 233 (1976). Maleimide derivatives can similarly be coupled to thiol-containing carriers [ibid]. Hydroxy derivatives can be attached to carriers using trichlorotriazine [Kay and Crook, *Nature* 216: 514 (1967)].

A multitude of other coupling techniques are available to those of ordinary skill in the art for joining the various derivatives of the present invention with conventional immunogenic carrier materials. For example, one skilled in the art can react an appropriate derivative with a bifunctional reagent such that one end thereof covalently couples with the derivative and the other end has a functional group for coupling to carriers as described above (e.g., amino, carboxyl, thiol, hydroxyl, and maleimido). For example, bifunctional coupling reagents are well known for coupling amine derivatives to amino-containing carriers (e.g., protein or polypeptide carriers) by toluene-2,4-diisocyanate [Hirs and Timasheff, *Methods in Enzymol.* 25 (Part B): 625 (1972)]; 4,4'-difluoro-3,3-dinitrodiphenyl sulfone [Cuatrecasas et al, *J. Biol. Chem.* 244: 406 (1969)]; glutaraldehyde [Frohman et al, *Endocrinol.* 87: 1055 (1970)]; bis-imidates [Dutton et al, *Biochem. Biophys. Res. Comm.* 23: 730 (1966)]; and chlorotriazine [Kay and Crook, *Nature* 216: 514 (1967)]. Other useful coupling reactions are thoroughly discussed in the literature [see Kopple, *Peptides and Amino Acids*, W. A. Benjamin, Inc. (New York 1966); Lowe and Dean, *Affinity Chromatography*, John Wiley & Sons (New York 1974); Means and Feeney, *Chemical Modification of Proteins*, Holden-Day (San Francisco 1971); and Glazer et al, *Chemical Modification of Proteins*, Elsevier (New York (1975)].

In formula (E) depicting the present immunogens, linking group R will comprise the R' linking group described above and the residue of functional group Z remaining after the coupling reaction. As previously detailed, the residue of functional group Z may be linked directly by a bond to an appropriate functional group on the carrier or may be linked through the residue of a bifunctional coupling reagent. Thus, as in the case of R', linking group R will vary widely and its exact chemical structure is not critical so long as it serves the purpose of linking the hapten residue without interfering with the immunogenic properties of the resulting immunogen. In particular, linking group R can be characterized by the same diversity of structure as described above for R'. The residue of functional group Z in the analyte derivative (B) preferably will be imino, carboxyl, sulfo, or oxy.

Particularly preferred are the immunogens of the formula:

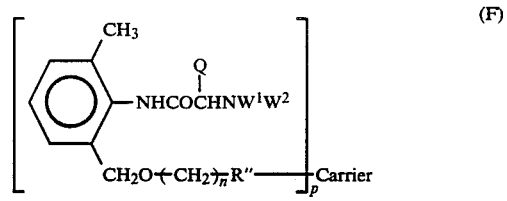

(F)

where R" is an appropriate linking group which can be of the same diversity as R' described in detail above and will normally be a chain of between 1 and 20 atoms, excluding hydrogen, also as described above with regard to R'. Conveniently, R" will be an amide group, i.e., —NHCO—, which can be oriented in either of the two possible ways, with the nitrogen atom in the amide group being from carrier amino groups and the carbon atom being from an appropriate derivative (e.g., a carboxylic acid), with p then representing the average number of coupled amino groups in the carrier (and preferably is as defined above), or with the nitrogen atom being from an appropriate derivative (e.g., an amino derivative) and the carbon atom being from carrier carboxyl groups, with p then representing the average number of coupled carboxyl groups in the carrier (and preferably is again as defined above).

ANTIBODIES

Preparation of specific antibodies using the present immunogen conjugates may follow any conventional technique. Numerous texts are available describing the fundamental aspects of inducing antibody formation, for example, reference may be made to Parker, *Radioimmunoassay of Biologically Active Compounds*, Prentice-Hall (Englewood Cliffs, N.J., U.S.A., (1976). In the usual case, a host animal such as a rabbit, goat, mouse, guinea pig, or horse is injected at one or more of a variety of sites with the immunogen conjugate, normally in mixture with an adjuvant. Further injections are made at the same site or different sites at regular or irregular intervals thereafter with bleedings being taken to assess antibody titer until it is determined that optimal titer has been reached. The host animal is bled to yield a suitable volume of specific antiserum. Where desirable, purification steps may be taken to remove undesired material such as nonspecific antibodies before the antiserum is considered suitable for use in performing actual assays.

The antibodies can also be obtained by somatic cell hybridization techniques, such antibodies being commonly referred to as monoclonal antibodies. Reviews of such monoclonal antibody techniques are found in *Lymphocyte Hybridomas*, ed. Melchers et al, Springer-Verlag (New York 1978), *Nature* 266: 495 (1977), *Science* 208: 692 (1980), and *Methods in Enzymology* 63 (Part B): 3–46 (1981).

IMMUNOASSAY TECHNIQUES

The antibodies prepared from the immunogens of the present invention can be used in any immunoassay method, and the corresponding reagent system, for determining lidocaine and its analogs, including agglutination techniques, radioimmunoassays, heterogeneous enzyme immunoassays (cf. U.S. Pat. No. 3,654,090), heterogeneous fluorescent immunoassays (cf. U.S. Pat. Nos. 4,201,763; 4,171,311; 4,133,639 and 3,992,631), and homogeneous (separation-free) immunoassays. The latter-most are particularly preferred and include such techniques as fluorescence quenching or enhancement (cf. U.S. Pat. No. 4,160,016), fluorescence polarization (cf. *J. Exp. Med.* 122: 1029 (1965), enzyme substrate-labeled immunoassay (cf. U.S. Pat. No. 4,279,992 and U.K. Pat. Specification No. 1,552,607), prosthetic group-labeled immunoassay (cf. U.S. Pat. No. 4,238,565), enzyme modulator-labeled immunoassay, e.g., using inhibitor labels (cf. U.S. Pat. Nos. 4,134,792 and 4,273,866), enzyme-labeled immunoassay (cf. U.S. Pat. No. 3,817,837), energy transfer immunoassay (cf. U.S. Pat. No. 3,996,345), and double antibody steric hindrance immunoassay (cf. U.S. Pat. Nos. 3,935,074 and 3,998,943). Homogeneous immunoassays, as is known in the art, are typically performed by setting up competition between the analyte and the labeled conjugate of the drug for binding to antibody and are characterized by the fact that the detectable label property is altered when the labeled conjugate is bound by antibody.

Moreover, the analyte derivatives (C) of the present invention can be used to prepare the labeled conjugates needed to perform the various immunoassays described above. Appropriate derivatives can be radio-labeled or labeled with fluorescent moieties in accordance with standard methods. Likewise the appropriate labeling moiety for the preferred homogeneous techniques, e.g., an enzyme substrate, a prosthetic group, and enzyme modulator, or an enzyme (which is a protein and can be coupled similarly to the immunogenic carrier as described above) can be coupled to the derivatives to yield labeled conjugates.

Particularly preferred labeled conjugates are the β-galactosyl-umbelliferone-labeled conjugates of the formula:

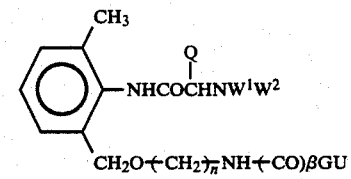

where Q, $W^1$, $W^2$, and n are described above, and —(CO)βGU is

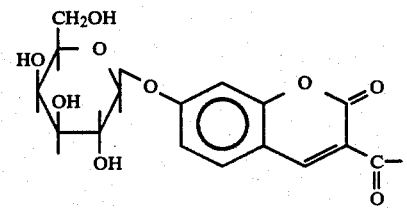

Such conjugates are prepared by standard peptide condensations of β-galactosyl-umbelliferone carboxylic acid (U.S. Pat. No. 4,226,978) with an appropriate amine-derivative of the analyte.

Another preferred labeled conjugate is that labeled with flavin adenine dinucleotide (FAD) which can be prepared by peptide condensation of an appropriate amino-derivative (B), $Z=NH_2$, with amino-FAD derivatives (see U.S. Pat. No. 4,213,893) using bifunctional reagents or with carboxyl-FAD derivatives. The resulting FAD conjugates are useful as label reagents in apoenzyme reactivation immunoassay systems (ARIS—See U.S. Pat. No. 4,238,565).

The reagent system or means of the present invention comprises all of the essential chemical elements required to conduct a desired immunoassay method encompassed by the present invention. The reagent system is presented in a commercially packaged form, as a composition or admixture where the compatibility of the reagents will allow, in a test device configuration, or as a test kit, i.e., a packaged combination of one or more containers holding the necessary reagents. Included in the reagent system are the reagents appropriate for the binding reaction system desired, e.g., an antibody and labeled conjugate of the present invention. Of course, the reagent system can include other materials as are known in the art and which may be desirable from a commercial and user standpoint, such as buffers, diluents, standards, and so forth. Particularly preferred is a test kit for the homogeneous competitive binding immunoassay of the present invention comprising (a) an antianalyte antibody of the present invention and (b) a labeled analyte conjugate which has a detectable property which is altered when bound with the antibody. Also preferred is a test device comprising a reagent composition including an antianalyte antibody of the present invention and a labeled analyte conjugate which has a detectable property which is altered when bound with the antibody, and a solid carrier member incorporated with the reagent composition. The various forms of such test device are described in commonly assigned U.S. patent application Ser. No. 202,378, filed Oct. 30, 1980, which is incorporated herein by reference and which has published as European patent application No. 51,213. The specific label used in the preferred test kit and test device will depend on the technique followed, as described hereinabove.

The present invention will now be illustrated, but is not intended to be limited, by the following examples:

EXAMPLES

REAGENTS

Italicized numbers appearing after chemical names refer to the structural formulas identified in the text above and/or in the drawings.

A. Preparation of drug derivative—N-[2-(3-Aminopropoxymethyl)-6-methylphenyl]-2-'-diethylaminoacetamide (7), $W^1=W^2=$ethyl, Q=hydrogen A mixture of 10 grams (g) [60 millimoles (mMol)] of 3-hydroxymethyl-2-nitrotoluene (1) (Aldrich Chemical Co., Milwaukee, WI) and 7.9 milliliters (ml) of acrylonitrile was stirred under argon at room temperature. Potassium tert-butoxide [10 milligrams (mg)] was added, followed 90 minutes later by an additional 10 mg portion. After a total of 3 hours, the reaction was quenched by the addition of 0.2 ml of acetic acid. Volatile material was removed under reduced pressure, and the residue chromatographed on 300 g of silica gel eluting with methylene chloride ($CH_2Cl_2$). Fractions of approximately 17 ml were collected. Fractions 155–200 were combined and the solvent evaporated to give 12.5 grams (g) (90% yield) of 3-(2-cyanoethoxymethyl)-2-nitrotoluene (2) as a clear oil.

$^1$H NMR Spectrum ($CDCl_3$): $\delta$7.38 (m, 3H, aromatic); 4.60 (s, 2H, $OCH_2$); 3.66 (t, J=6 Hz, 2H, $CH_2$); 2.60 (t, J=6 Hz, 2H, $CH_2$); 2.30 (s, 3H, $CH_3$).

Infrared Spectrum (neat): 2360 cm$^{-1}$ (CN).

A solution of 12 g (55 mMol) of the nitro compound (2) in 140 ml of glacial acetic acid was combined with 550 mg of platinum dioxide ($PtO_2$) and shaken at room temperature under a hydrogen atmosphere of 50 pounds per square inch (psi) for 6 hours. It was then filtered to remove the catalyst and the solvent was evaporated under reduced pressure. The residue was dissolved in 100 ml of n-butanol and the solution washed twice with 50 ml of saturated aqueous sodium bicarbonate solution. The aqueous washes were combined and extracted two 75 ml portions of n-butanol. The combined butanol extracts were combined, dried over anhydrous sodium sulfate ($Na_2SO_4$), and evaporated. The oily residue was purified on a preparative liquid chromatograph using silica gel as the adsorbent and eluting with 40:10:1 (v/v/v) chloroform ($CHCl_3$):methanol:conc. ammonium hydroxide. This yielded 3.15 g (30% yield) of 2-(3-aminopropoxymethyl)-6-methylaniline (3) as an oil.

$^1$H NMR Spectrum ($d_6$ DMSO): $\delta$7.0–64 (m, 3H, aromatic); 4.40 (s, 2H, $OCH_2$); 3.45 (t, 2H, J=6 Hz, $OCH_2$); 2.62 (t, 2H, J=7 Hz, $CH_2$); 2.1 (s, 3H, $CH_3$), 1.60 (t, 2H, J=6 Hz, $CH_2$).

Mass Spectrum (EI): m/e 194 [M+]

To a solution of 7.3 g (38 mMol) of the diamine (3) in 125 ml of chloroform ($CHCl_3$) was added 8.28 g (0.38 mMol) of di-tert butyl dicarbonate in 25 ml of $CHCl_3$. The reaction was allowed to stir for 45 minutes at room temperature under argon, then concentrated under reduced pressure to yield 11.8 g (100%) of 2-(3-tert-butyloxycarbonylaminopropoxymethyl)-6-methylaniline (4) as an orange oil.

$^1$H NMR Spectrum ($CDCl_3$): $\delta$7.2–6.8 (m, 3H, aromatic); 4.53 (s, 2H, $OCH_2$); 3.48 (t, 2H, J=6 Hz, $CH_2$); 3.17 (t, 2H, J=7 Hz, $CH_2$); 1.17 (s, 3H, $CH_3$); 1.75 (t, 2H, $CH_2$); 1.50 (s, 9H, $C_4H_9$).

Mass Spectrum (EI): m/e 294 [M+].

This oil was not further purified. It was combined with 60 ml of aqueous 1.75M sodium acetate solution and 46 ml of acetic acid. The mixture was cooled to 10° C. and 6.22 g (44 mMol) of bromoacetyl chloride was added dropwise over 2 minutes. After 5 more minutes, an additional 3.1 g (22 mMol) of the acid chloride was added and stirring continued for 30 minutes. The reaction was diluted with 350 ml of $CHCl_3$, and this washed once with 150 ml of water ($H_2O$) and twice with 200 ml of saturated sodium bicarbonate ($NaHCO_3$) solution. The organic phase was separated, dried over anhydrous $Na_2SO_4$, filtered, and concentrated to give 13.2 g (84% yield) of the bromo compound (5) as a viscous orange oil. It was dissolved in 95 ml of toluene and 7.0 g (96 mMol) of diethylamine was added. After stirring for 18 hours at room temperature, the mixture was filtered and washed with 50 ml of $H_2O$. The organic phase was dried over anhydrous $Na_2SO_4$, filtered, and evaporated. The residue was purified on a preparative liquid chromatograph using silica gel as the adsorbent and eluting with 9:1 (v/v) $CHCl_3$:acetone. This gave 6 g [39% yield overall from (3)] of N-[2-(3-tert-butyloxycarbonylaminopropoxymethyl)-6-methylphenyl]-2'-diethylaminoacetamide (6), $W^1=W^2=$ethyl, Q=H, as a yellow oil.

$^1$H NMR Spectrum ($CDCl_3$): $\delta$7.20 (s, 3H, aromatic); 4.47 (s, 2H, $CH_2$); 3.50 (s, 2H, $CH_2$); 3.23 (s, 2H, $CH_2$); 3.20 t, 2H, $CH_2$); 2.70 (q, J=8 Hz, 4H, 2 $CH_2$); 2.26 (s, 3H, $CH_3$); 1.40 (s, 9H, $C_4H_9$); 1.17 (t, J=8 Hz, 6H, 2 $CH_3$).

Mass Spectrum (CI): m/e 408 [MH+]

The carbamate (6) was stirred with 115 ml of 1 normal (N) hydrochloric acid (HCl) at room temperature for 2.5 hours. The reaction was then concentrated under reduced pressure and the residue chromatographed on 325 g of silica gel eluting with 60:10:1 (v/v/v) $CHCl_3$:methanol:concentrated ammonium hydroxide. Twenty ml fractions were collected. Fractions 73–145 were pooled and the solvent removed. The residue was converted to the HCl salt by dissolving in HCl-2-propanol (3.9M) and evaporating to dryness. This gave, after drying at 58° C. under high vacuum, 3.3 g (59% yield) of the drug derivative (7), $W^1=W^2=$ethyl, Q=H, as a hydroscopic powder.

Calculated for $C_{17}H_{31}Cl_2N_3O_2$: C, 53.68; H, 8.22; N, 11.05. Found: C, 53.85; H, 8.35; N, 10.83.

Mass Spectrum (CI): m/e 308 [M+1].

B. Preparation of immunogen and antibody

A solution was prepared by dissolving 230 mg of bovine serum albumin (BSA) in 36 ml of distilled $H_2O$. To it was added 379 mg of the amino-functionalized lidocaine derivative from Part A above and the pH was lowered to 4.8 with 1N HCl. This solution was cooled and stirred while 1.28 g of solid 1-ethyl-3-(3-dimethylaminopropyl)carbodiimide hydrochloride was added. The pH was adjusted to 4.8 with 0.1N HCl and the reaction stirred at 0° C. for one hour. The pH was carefully raised to 6.0 first with 0.1N sodium hydroxide (NaOH) then with 0.02N NaOH and the solution held at 0° C. for 3 hours, then allowed to stand overnight in the refrigerator (4° C.). The solution, now about 40 ml in volume, was brought to room temperature and applied to a 0.05 cm×26 cm column of Sephadex G-25 (Pharmacia, Piscataway, NJ) equilibrated in 0.2M sodium chloride (NaCl). The column was eluted with 0.2M NaCl at a flow rate of 1 ml/min. and fractions of 15 ml volume were collected. Fractions 16–22 were pooled to give 262 mg of recovered protein as measured by the Lowry method [Lowry et al, J. Biol. Chem. 193: 265 (1951)]. The average number of lidocaine haptens conjugated to each protein molecule (epitope density) was determined by titration of the unreacted carboxyl groups on the protein and found to be 18.

The lidocaine immunogen was filtered through a 0.8 micron membrane filter and diluted to 1.0 mg/ml with 0.2M NaCl. Six ml of immunogen (1 mg/ml) was combined with 12 ml of Fruends complete adjuvant and 6 ml of saline. Rabbits were immunized simultaneously each with 2 ml of this mixture. Three weeks later they were reimmunized with the same mixture prepared with incomplete Fruends adjuvant. The booster immunizations were repeated every four weeks. Test bleedings were taken one week after the boosters. Antisera with suitable titers were obtained by three months after the initial immunizations.

C. Preparation of labeled conjugate

To a solution of 176 mg (0.44 mMol) of 7-β-galactosylcoumarin-3-carboxylic acid [Burd et al, Clin. Chem. 23: 1402 (1977)] and 44 mg (0.44 mMol) of triethylamine in 5 ml of dry dimethylformamide at 0° C. was added 60 mg of isobutyl chloroformate. After stirring for 15 minutes at this temperature, the reaction was combined with 140 mg (0.37 mMol) of the dihydrochloride salt of the drug derivative from Part A of this Example and 88 mg of triethylamine in 5 ml of dry dimethylformamide. After stirring for an additional 45 minutes, the solvent was removed on a rotary evaporator attached to a vacuum pump. The residue was chromatographed on 75 g of silica gel eluting with absolute ethanol and collecting approximately 17 ml fractions. Fractions 15–30 were pooled and the solvent removed. This residue was re-chromatographed on Sephadex LH-20 (Pharmacia) (2.5×54 cm) eluting with methanol. This yielded 108 mg (44%) of the conjugate as a cream colored, glassy solid.

Calculated for $C_{33}H_{43}N_3O_{11}$: C, 60.27; H, 6.54; N, 6.39. Found: C, 60.07; H, 6.70; N, 6.15.

Mass Spectrum (FAB): m/e 658 [M+1].

IMMUNOASSAY METHOD

A homogeneous substrate-labeled fluorescent immunoassay (SLFIA—U.S. Pat. No. 4,279,992) for lidocaine was established as follows:

A. Reagents

1. Antibody/Enzyme Reagent—50 mM Bicine buffer [N,N-bis-(2-hydroxyethyl)glycine, Calbiochem-Behring Corp., LaJolla, CA], pH 8.3 containing 0.10 units/ml β-galactosidase, sufficient antiserum from Part B of this Example to decrease fluorescence to 20% of that in the absence of antiserum, and 15.4 mM sodium azide.

2. Conjugate Reagent—30 mM formate buffer, pH 3.5, and 0.010 $A_{343}$ (absorbance units at 343 nm) units of the labeled conjugate from Part C of this Example.

3. Lidocaine Standards—USP Reference Standard lidocaine added to normal human serum; diluted 51-fold with 50 mM Bicine buffer, containing 15.4 mM sodium azide.

B. Inhibition of Hydrolysis of β-GU-Lidocaine by Antiserum to Lidocaine

Increasing amounts of antiserum were added to 1.5 ml of Bicine buffer containing 0.10 units/ml β-galactosidase. The reactions were initiated with 50 μl of the Conjugate Reagent added to each cuvette with mixing. After 20 minutes the fluorescence intensity was measured in each cuvette (excitation 400 nm, emission 450 nm). The results are presented below:

| μl Antiserum | Fluorescence |
| --- | --- |
| 0 | 8.59 |
| 1 | 4.84 |
| 2 | 2.02 |
| 4 | 1.09 |
| 7 | 0.93 |
| 10 | 0.95 |

C. Lidocaine Assay Method and Results

To 1.5 ml of the Antibody/Enzyme Reagent in cuvettes were added 50 μl (microliters) of the diluted lidocaine standards. Then to begin the reaction, 50 μl of the Conjugate Reagent was added to each cuvette with mixing. After 20 minutes the fluorescence intensity was measured in each cuvette (excitation 400 nm, emission 450 nm).

Performance of the assay yielded the following results:

| μg/ml Lidocaine | Fluorescence |
| --- | --- |
| 0 | 2.49 |
| 1 | 2.96 |
| 4 | 4.74 |
| 8 | 7.11 |
| 12 | 8.47 |

The immunoassay could thus be used to determine lidocaine concentrations in serum samples.

Of course, many other modifications or variations of the invention set forth above can be made without departing from the spirit and scope hereof.

What is claimed is:

1. An immunogen compound comprising one or more residues of the formula:

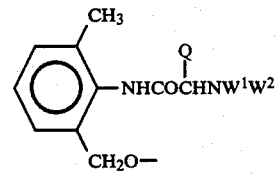

wherein Q is selected from the group consisting of hydrogen and lower alkyl, $W^1$ and $W^2$ can be the same or different and are selected from the group consisting of hydrogen and lower alkyl, chemically linked to an immunogenic carrier material.

2. The immunogen of claim 1 wherein the carrier material is a protein or a polypeptide.

3. The immunogen of claim 1 wherein the one or more residues are covalently linked to the carrier material by a chain comprising between 1 and 20 atoms, excluding hydrogen.

4. The immunogen of claim 1 wherein Q is hydrogen and $W^1$ and $W^2$ are both ethyl.

5. The immunogen of claim 1 wherein there are on the average less than about 50 of the residues linked to the carrier material.

6. An immunogen compound of the formula

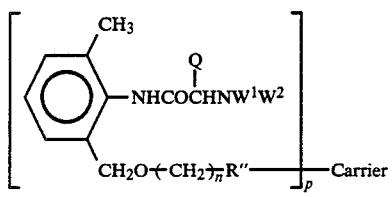

wherein Q is selected from the group consisting of hydrogen and lower alkyl, $W^1$ and $W^2$ can be the same or different and are selected from the group consisting of hydrogen and lower alkyl, n is an integer from 1 through 10, R" is a linking group, n is on the average from 1 to the number of available coupling sites on Carrier, and Carrier is an immunogenic carrier material.

7. The immunogen of claim 6 wherein R" is a linking group consisting of a chain of between 1 and 20 atoms, excluding hydrogen.

8. The immunogen of claim 6 wherein the carrier material is a protein or a polypeptide.

9. The immunogen of claim 8 wherein R" is an amide group coupling through amino or carboxyl groups on the carrier material.

10. The immunogen of claim 6 wherein Q is hydrogen and $W^1$ and $W^2$ are both ethyl.

11. The immunogen of claim 6 wherein n is 3.

12. The immunogen of claim 6 wherein p is less than 50.

13. An antibody prepared against the immunogen of claim 1.

14. An antibody prepared against the immunogen of claim 6.

15. An antibody prepared against the immunogen of claim 9.

16. In an immunoassay method for determining lidocaine in a test sample, wherein the test sample is contacted with an antibody to lidocaine and with a labeled conjugate comprising lidocaine or a binding analog of lidocaine and a label, and wherein thereafter the relative amount of the labeled conjugate that becomes bound to the antibody is determined, the improvement which comprises employing the antibody of claim 13, wherein Q is hydrogen and $W^1$ and $W^2$ are both ethyl, as the antibody to lidocaine.

17. In a reagent system for determining lidocaine by immunoassay, the improvement which comprises employing the antibody of claim 13, wherein Q is hydrogen and $W^1$ and $W^2$ are both ethyl, as the antibody to lidocaine.

18. A β-galactosyl-umbelliferone-labeled conjugate of the formula:

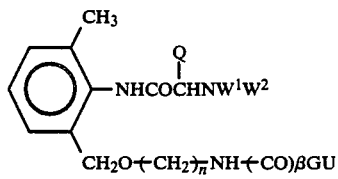

wherein Q is selected from the group consisting of hydrogen and lower alkyl, $W^1$ and $W^2$ can be the same or different and are selected from the group consisting of hydrogen and lower alkyl, n is an integer from 1 through 10, and —(CO)βGU is

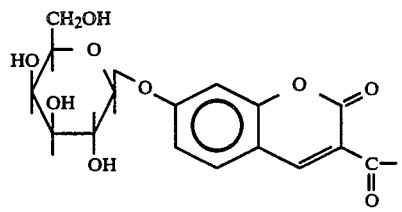

19. The conjugate of claim 18 wherein Q is hydrogen and $W^1$ and $W^2$ are both ethyl.

20. The conjugate of claim 19 wherein n is 3.

21. A compound of the formula:

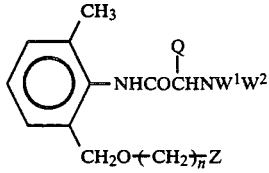

wherein Q is hydrogen or lower alkyl, $W^1$ and $W^2$, which can be the same or different, are selected from hydrogen and lower alkyl, n is an integer from 1 through 10, and Z is amino or carboxyl.

22. The compound of claim 21 wherein Q is hydrogen and $W^1$ and $W_2$ are both ethyl.

23. The compound of claim 21 wherein Q is methyl and $W^1$ and $W^2$ are both hydrogen.

24. The compound of claim 21 wherein Z is amino.

25. The compound of claim 24 wherein n is 3.

* * * * *

UNITED STATES PATENT AND TRADEMARK OFFICE
CERTIFICATE OF CORRECTION

PATENT NO. : 4,650,771

DATED : March 17, 1987

INVENTOR(S) : Robert T. Buckler, et al.

It is certified that error appears in the above–identified patent and that said Letters Patent are hereby corrected as shown below:

Column 15, line 27, after "group,", please delete "n" and insert --p-- in place thereof.

Signed and Sealed this

Twentieth Day of September, 1988

Attest:

DONALD J. QUIGG

Attesting Officer

Commissioner of Patents and Trademarks